United States Patent [19]

Ikeda et al.

[11] 4,297,872

[45] Nov. 3, 1981

[54] VIBRATION TYPE TRANSDUCER

[75] Inventors: Kyoichi Ikeda; Motoyoshi Ando, both of Musashino, Japan

[73] Assignee: Yokogawa Electric Works, Ltd., Tokyo, Japan

[21] Appl. No.: 108,477

[22] Filed: Dec. 31, 1979

[30] Foreign Application Priority Data

Jan. 11, 1979 [JP] Japan ............................. 54-2089

[51] Int. Cl.³ ...................... G01N 9/00; G01L 11/00; G01H 13/00
[52] U.S. Cl. ..................................... 73/32 A; 73/579; 73/702
[58] Field of Search .......... 73/32 A, 579, 581, 339 A, 73/702, 704, 708, 517 AV, DIG. 1, 290 V

[56] References Cited

U.S. PATENT DOCUMENTS

| 3,449,941 | 6/1969 | Banks | 73/32 A |
| 3,540,265 | 11/1970 | Lynnworth | 73/339 A X |
| 3,603,137 | 9/1971 | Banks | 73/32 A |
| 3,975,948 | 8/1966 | Makino | 73/581 |
| 4,086,809 | 5/1978 | Wu | 73/DIG. 1 |

FOREIGN PATENT DOCUMENTS 2027539A  2/1980  United Kingdom ............... 73/32 A Primary Examiner—James J. Gill
Attorney, Agent, or Firm—Parmelee, Johnson, Bollinger & Bramblett

[57] ABSTRACT

A vibration type transducer is provided in which various physical quantities, for example, the pressure, density, force and temperature are measured from the natural frequencies of the mechanically vibrated vibrator.

The vibrating element is vibrated in a plurality of vibration modes and a plurality of resultant frequency signals are processed to obtain signals associated with the various physical quantities. The system is not influenced by physical quantity other than the physical quantity to be measured.

8 Claims, 12 Drawing Figures

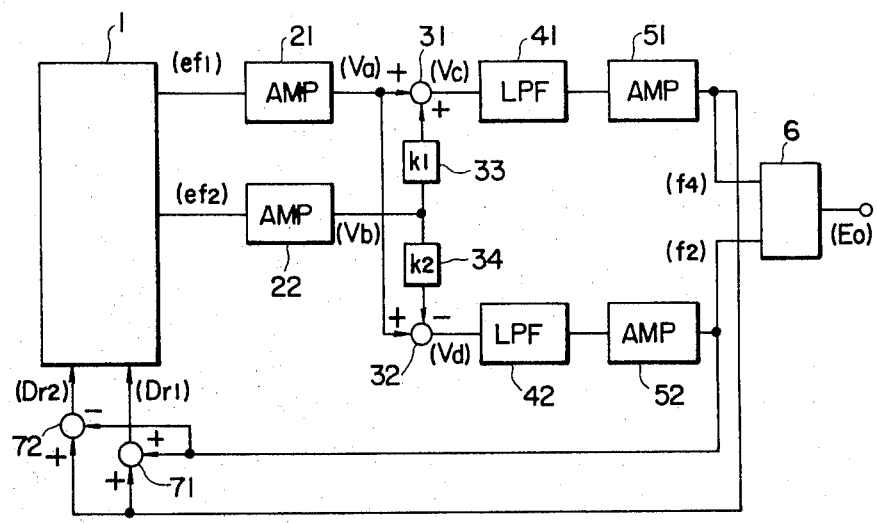
FIG. 1
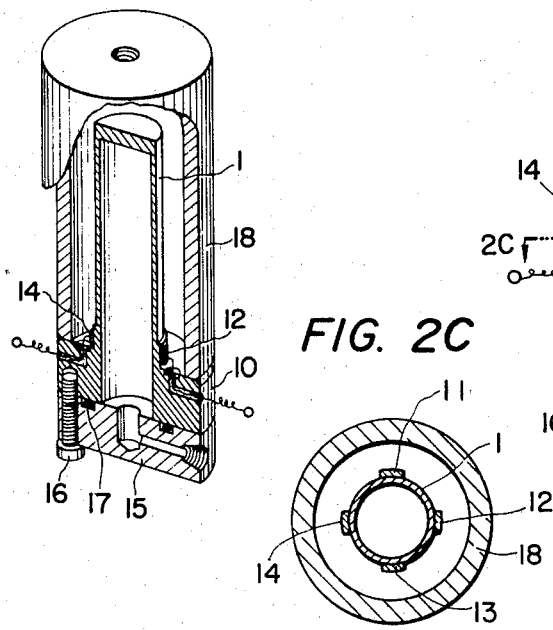
FIG. 2A
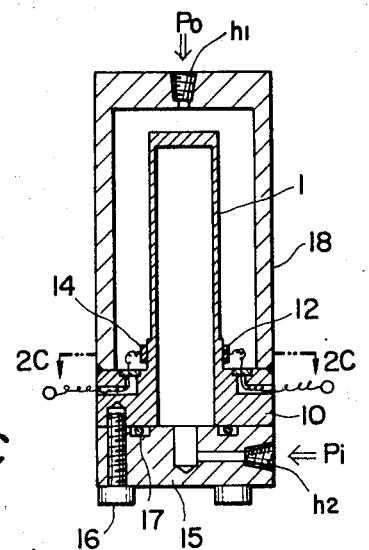
FIG. 2B
FIG. 2C

VIBRATION TYPE TRANSDUCER

BACKGROUND OF THE INVENTION

1. Field of the Invention

This invention relates to a vibration type transducer wherein various physical quantities of a fluid introduced around a vibrating element, such as the pressure, differential pressure, temperature and density thereof, are converted into frequency signals corresponding to the physical quantities, and the frequency signals are processed to make the various physical quantities known. The vibration type transducer is extensively applicable to, for example, a pressure gauge, differential pressure gauge, density meter and thermometer.

2. Description of the Prior Art

An example of a vibration type transducer which detects vibration frequency signals of a vibrating element so as to measure various physical quantities, is described in 'INSTRUMENT PRACTICE', August 1964, pp. 823-829. In this transducer, a vibrating cylinder is employed as the vibrating element. Pressures are introduced inside and outside the cylinder, and the differential pressure is detected from the vibration frequency of the cylinder. Such prior art apparatus for measuring the differential pressure has the disadvantage that the vibration frequency is influenced by the temperature or density of the fluid to be measured.

SUMMARY OF THE INVENTION

It is an object of the present invention to provide a new and novel vibration transducer system capable of measuring a physical quantity which measurement is not subjected to the influence of any other physical quantity.

In carrying out this invention in one illustrative embodiment thereof a vibrator has a vibration drive means for simultaneously or time division vibrating said vibrator in a plurality of vibration modes. Vibration detection means are provided for detecting the vibrations of said vibrator and the detected signals are processed to provide a signal relating to a physical property which is to be measured.

BRIEF DESCRIPTION OF THE DRAWINGS

The invention, together with further objects, aspects and advantages thereof, will be more clearly understood from the following description taken in conjunction with the accompanying drawings.

FIG. 1 is a schematic block diagram of a vibration type transducer embodied in this invention.

FIGS. 2A, 2B and 2C are constructional views showing an example of a vibrating element for use in the apparatus of this invention, in which FIG. 2A is a perspective view partially in section, FIG. 2B is a vertical sectional view and FIG. 2C is a sectional view taken along line 2C in FIG. 2B.

DESCRIPTION OF THE PREFERRED EMBODIMENTS

Figure 3:
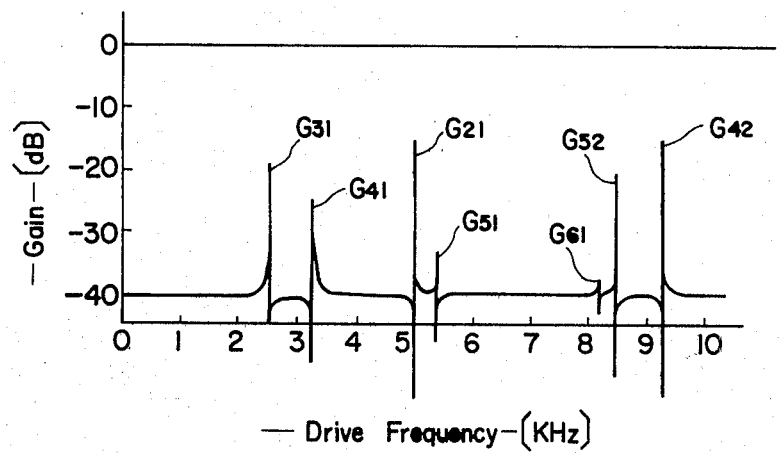
FIG. 3 is a graph showing typical drive frequency-gain characteristics of the vibrating element shown in FIGS. 2A through 2C which is in the shape of a cylinder closed at one end.

Referring now to FIG. 1, a vibrating element or vibrator, referred to generally with the reference number 1, generates signals $e_{f1}$ and $e_{f2}$ corresponding to natural frequencies $f_1$ and $f_2$ in at least two vibrational modes. The frequency signals $e_{f1}$ and $e_{f2}$ are applied to amplifiers 21 and 22, respectively and amplified therein. An output signal $v_a$ of the amplifier 21 is applied to an adder circuit 31 and a subtracter circuit 32, while an output signal $v_b$ of the amplifier 22 is applied to the adder circuit 31 and the subtracter circuit 32 through respective coefficient circuits 33 and 34 for multiplying this signal by coefficients $k_1$ and $k_2$. The adder circuit 31 adds the output signal $v_a$ of the amplifier 21 and the output signal $v_b$ of the amplifier 22 applied through the coefficient circuit 33. The resultant addition output $v_c = (v_a + k_1 \cdot v_b)$ is applied to an arithmetic circuit 6 through a low-pass filter 41 and an amplifier 51, the low-pass filter being adapted to pass frequencies of, e.g., at most 6 KHz.

The subtracter circuit 32 subtracts the output signal $v_b$ of the amplifier 22 applied through the coefficient circuit 34, from the output signal $v_a$ of the amplifier 21. The resultant subtraction output $v_d = (v_a - k_2 \cdot v_b)$ is applied to the arithmetic circuit 6 through a low-pass filter 42 and an amplifier 52, the low-pass filter being adapted to pass frequencies of, e.g., at most 6 KHz.

An adder circuit 71 adds output signals of the amplifiers 51 and 52, and applies the resultant addition signal $D_{r1}$ to the vibrator 1 so as to vibrate this vibrator in, for example, the second order vibration mode. A subtracter circuit 72 subtracts the output signal of the amplifier 52 from the output signal of the amplifier 51, and applies the resultant subtraction signal $D_{r2}$ to the vibrator 1 so as to vibrate this vibrator in, for example, the fourth order vibration mode.

Accordingly, two closed loops are formed including the amplifiers 21 and 22, the adder circuit 31, the subtracter circuit 32, the low-pass filters 41 and 42, the amplifiers 51 and 52, the adder circuit 71, the subtracter circuit 72 and the vibrator 1 constituting a driver circuit which simultaneously vibrates the vibrator 1 in the second order and the fourth order vibrational modes. The arithmetic circuit 6 receives as inputs a frequency signal $f_4$ delivered from the amplifier 51 and associated with the fourth order vibration mode of the vibrator 1 and a frequency signal $f_2$ delivered from the amplifier 52 and associated with the second order vibration mode of the vibrator 1. Arithmetic circuit 6 processes the input signals to provide an output signal $E_o$ corresponding to a physical quantity to be measured.

FIGS. 2A, 2B and 2C illustrates one type of vibrator which may be used in the apparatus of this invention. In this embodiment, the vibrator 1 is constructed in the shape of a cylinder with one end closed. A fluid under a pressure $P_i$ is introduced inside the cylinder vibrator 1, and a fluid under pressure $P_o$ surrounds the outside of the vibrator so as to create a differential pressure in the vibrator. Piezoelectric elements 11 and 12 for detecting frequencies, and piezoelectric elements 13 and 14 for driving the vibrator are respectively mounted on the peripheral outer wall of the cylindrical vibrator 1 spaced 90 degrees from each other with respect to the axis of the cylindrical vibrator 1. The cylindrical vibrator 1 has a mounting flange 10, which is fixed to a body 15 by means of a bolt 16. An O-ring 17 is interposed between the flange 10 and the body 15 so as to seal the interface between these components. The vibrator 1 is enclosed with a cylindrical vessel 18 which is fixed to the flange 10. The fluid under the pressure $P_o$ is introduced from a pressure hole $h_1$ provided in the cylindrical vessel 18 into the interspace between the vibrator 1 and the vessel 18, that is, around the outside of vibrator 1. On the other hand, the fluid under pressure $P_i$ is introduced from a pressure hole $h_2$ provided in the body 15 into the space inside the vibrator 1.

FIG. 3 is a graph which illustrates typical drive frequency-gain characteristics of the cylindrical vibrator as shown in FIGS. 2A through 2C. Gain characteristics expressed in decibels were obtained in accordance with the ratio of an output of the vibration detecting piezoelectric element (which is always stuck to a position where the maximum amplitude is provided) to an applied voltage to the driving piezoelectric element in which each drive for the vibrator and the detection of the vibrations from the vibrator is provided by a single piezoelectric element. In FIG. 3, $G_{31}$, $G_{41}$, $G_{21}$, $G_{51}$ and $G_{61}$ denote gains in the case where vibration modes within a plane are of the third order, fourth order, second order, fifth order and sixth order, respectively, and where all vibration modes in an axial direction are of the first order. $G_{52}$ and $G_{42}$ denote gains in the case where intraplanar vibration modes are of the fifth order and fourth order, respectively, and where both axial vibration modes are of the second order. Accordingly, when the vibrator 1 is supplied by a drive signal having a frequency at a point at which the gain rises remarkably, it can be vibrated in a desired vibration mode.

Figure 4:
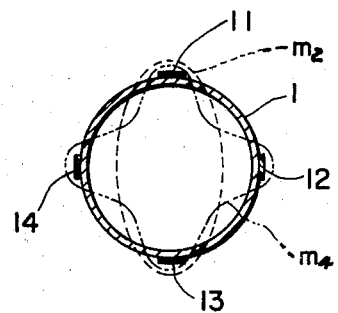
FIG. 4 is a view for explaining the vibrating states of the vibrating element of FIGS. 2A through 2C in the second order and fourth order vibration modes.

The operation of FIG. 1 employing the cylindrical vibrator 1 having the construction as shown in FIGS. 2A through 2C and exhibiting the characteristics as shown in FIG. 3 will now be described. The circuit of FIG. 1 is so constructed that when a signal of the same frequency as the natural frequency in the fourth order vibration mode is applied to the vibrator 1, almost no phase difference occurs between the signal derived from the amplifier 51 and the applied signal. Further, that when a signal of the same frequency as the natural frequency in the second order vibration mode is applied to the vibrator 1, almost no phase difference occurs between the signal derived from the amplifier 52 and the applied signal. In the case where the low-pass filters 41 and 42 are designed in advance so as to permit frequency signals of at most 6 KHz to pass, signals to be passed include frequency signals associated with the third order and fifth order vibration modes in addition to the frequency signals associated with the second order and fourth order vibration modes. The signal components associated with the third order and fifth order vibration modes, however, are made irrelevant to the vibrations of the vibrator 1 by the mounting positions of the driving piezoelectric elements 13 and 14 and the vibration detecting piezoelectric elements 11 and 12. Accordingly, assuming that the vibrator 1 is vibrating simultaneously in the second order vibration mode $m_2$ and the fourth order vibration mode $m_4$ as shown in FIG. 4 under the steady state operation (the parts of the piezoelectric elements become the loops of the vibrations), signals $v_a$ and $v_b$ are respectively provided from the amplifiers 21 and 22 as follows:

$$v_a = m_2 + m_4 \qquad (1)$$
$$v_b = -m_2' + m_4'$$

where
$m_2$, $-m_2'$: signal components caused by the second order vibration mode,
$m_4$, $m_4'$: signal components caused by the fourth order vibration mode.

The coefficient circuits 33 and 34 are constructed so as to multiply the output signal $v_b$ of the amplifier 22 by values $m_2/m_2'$ and $m_4/m_4'$, respectively (since $m_2$ and $m_2'$ denote the signal components of the identical mode and $m_4$ and $m_4'$ denote the signal components of the identical mode, it can be said that these ratios are constant). Accordingly, the respective output signal $v_c$ and $v_d$ of the adder circuit 31 and the subtracter circuit 32 become as follows:

$$\begin{aligned} v_c &= v_a + \frac{m_2}{m_2'} \cdot v_b \\ &= m_4 + k \cdot m_4' \\ v_d &= v_a - \frac{m_4}{m_4'} \cdot v_b \\ &= m_2 + k' \cdot m_2' \end{aligned} \qquad (2)$$

where $k$, $k'$: coefficient values of the respective coefficient circuits 33 and 34 ($m_2/m_2'$ and $m_4/m_4'$).

As will be apparent from Equations (2), the outputs $v_c$ and $v_d$ become signals which correspond only to the fourth order and second order vibration modes, respectively. The signals $v_c$ and $v_d$ are applied to the arithmetic circuit 6 through the low-pass filters 41 and 42 and the amplifiers 51 and 52. Further, the adder circuit 71 and the subtracter circuit 72 having received these signals, apply voltages to the piezoelectric elements 13 and 14 which vibrate the vibrator 1 in the second order and fourth order vibration modes without fail. In this embodiment, the detection of the vibrations of the vibrator 1 is made only on the signals caused by the second order and fourth order vibration modes, and besides, the drive of the vibrator 1 is made by subjecting the vibrator 1 to compulsory forces deforming the vibrator in the second order and fourth order vibration modes, so that the vibrator 1 is vibrated in the two vibration modes (of the second order and fourth order) in a very stable state. When the frequency $f_2$ concerning the second order vibration mode and the frequency $f_4$ concerning the fourth order vibration mode of the vibrator 1 are indicated as functions of the pressure P, Equations (3) hold:

$$f_2 = C_2 \sqrt{\frac{E \cdot I \cdot (l + \beta_2 \cdot P)}{\rho \cdot A \cdot \left(l + \alpha_2 \cdot \frac{px}{\rho}\right)}} \qquad (3)$$

$$F_4 = C_4 \sqrt{\frac{E \cdot I \cdot (l + \beta_4 \cdot P)}{\rho \cdot A \cdot \left(l + \alpha_4 \cdot \frac{px}{\rho}\right)}}$$

where
- $C_2$, $C_4$: constants which are respectively determined by the second order and fourth order vibration modes,
- E: Young's modulus of the vibrator 1 (thin-walled cylindrical portion),
- A: cross-sectional area of the vibrator 1,
- l: length of the vibrator 1,
- I: second moment of area of the vibrator 1,
- $\rho$: density of the vibrator 1,
- $\rho_x$: density of the fluid surrounding the vibrator 1,
- $\alpha_2$, $\alpha_4$: fluid density-sensitivity coefficients in the second order and fourth order vibration modes respectively,
- $\beta_2$, $\beta_4$: pressure sensitivity coefficients in the second order and fourth order vibration modes respectively,
- P: pressure to be measured (differential pressure $P_i - P_o$ between the pressure $P_i$ introduced into the pressure hole $h_2$ and the surrounding pressure $P_o$).

When Equations (3) have $\rho_x$ eliminated therefrom and are arranged with respect to P, Equation (4) can be obtained:

$$P = \frac{(\alpha_4 - \alpha_2) - \left(\frac{C_2' \cdot \alpha_4}{f_2^2} - \frac{C_4' \cdot \alpha_2}{f_4^2}\right)}{\frac{C_2' \cdot \alpha_4 \cdot \beta_2}{f_2^2} - \frac{C_4' \cdot \alpha_2 \cdot \beta_4}{f_4^2}} = \frac{\alpha_4 - \alpha_2}{\frac{C_2' \cdot \alpha_4 \cdot \beta_2}{f_2^2} - \frac{C_4' \cdot \alpha_2 \cdot \beta_4}{f_4^2}} \tag{4}$$

$$\left(\because |\alpha_4 - \alpha_2| \gg \left|\frac{C_2' \cdot \alpha_4}{f_2^2} - \frac{C_4' \cdot \alpha_2}{f_4^2}\right|\right)$$

where $$C_2' = \frac{E \cdot I}{\rho \cdot A} \cdot C_2{}^2$$

$$C_4' = \frac{E \cdot I}{\rho \cdot A} \cdot C_4{}^2$$

Here, $\alpha_4 - \alpha_2$, $C_2' \cdot \alpha_4 \cdot \beta_2$ and $C_4' \cdot \alpha_2 \cdot \beta_4$ are constant and are respectively represented by $D_o$, $A_o$ and $B_o$. Then, Equation (4) becomes Equation (5) below.

$$P = \frac{D_o}{\frac{A_o}{f_2^2} - \frac{B_o}{f_4^2}} \tag{5}$$

The values of $D_o$, $A_o$ and $B_o$ can be readily determined by setting three different pressures (reference pressures) P and evaluating the frequencies $f_2$ and $f_4$ at that time (corresponding to the frequencies of the output signals of the respective amplifiers 52 and 51). Accordingly, when the invariables $D_o$, $A_o$ and $B_o$ are evaluated by this method in advance, the magnitude of the pressure to be measured is known on the basis of Equation (5) from the frequencies $f_2$ and $f_4$ of the vibrator 1 at the application of the pressure to be measured. Upon receiving the signals relevant to the frequencies $f_2$ and $f_4$ derived from the amplifiers 51 and 52, the arithmetic circuit 6 executes the processing indicated by Equation (5) and thereby provides the signal $E_o$ corresponding to the pressure to be measured P.

Since the pressure gauge of such construction obtains the frequencies $f_2$ and $f_4$ of the two vibration modes from the vibrator 1 and assesses the pressure to be measured on the basis of Equation (5), in principle as will be apparent from Equation (5), any error caused by a change in the fluid density $\rho_x$ does not occur.

Figure 5:
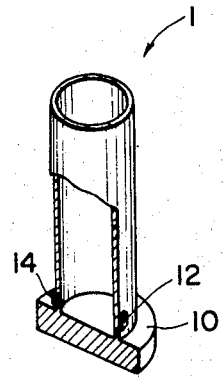
FIGS. 5 through 7 are perspective views each showing another example of a vibrating element for use in this invention.
Figure 6:
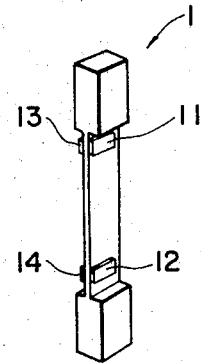
Figure 7:
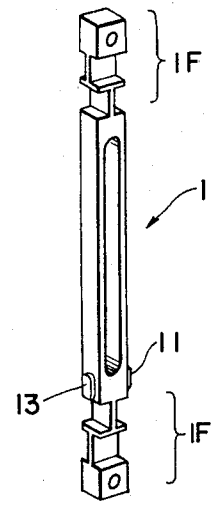

FIGS. 5 through 7 are perspective views showing examples of the type of vibrator 1 which may be used in the apparatus of this invention.

The vibrator shown in FIG. 5 is in the shape of a cylinder having one end open. By inserting the cylindrical vibrator into a fluid to be measured, the density of the fluid can be measured.

More specifically, the natural frequency $f_2$ concerning the second order vibration mode and the natural frequency $f_4$ concerning the fourth order vibration mode of the cylindrical vibrator 1, open at one end, are represented by Equations (6) as functions of the density $\rho_x$:

$$f_2 = C_2 \sqrt{\frac{E \cdot I_2}{A \cdot l^4 \cdot (\rho + \alpha_2 \cdot \rho_x)}} \tag{6}$$

$$f_4 = C_4 \sqrt{\frac{E \cdot I_4}{A \cdot l^4 \cdot (\rho + \alpha_2 \cdot \rho_x)}}$$

where
- $C_2$, $C_4$: constants which are respectively determined by the second order and fourth order vibration modes,
- l: length of the cylindrical vibrator 1,
- $I_2$, $I_4$: second moments of area of the cylindrical vibrators 1 as are respectively determined by the second order and fourth order vibration modes.

Here, $f_4/f_2$ is obtained as in the following Equation (7):

$$\frac{f_4}{f_2} = \frac{C_4}{C_2} \sqrt{\frac{I_4 \cdot (\rho + \alpha_2 \cdot \rho_x)}{I_2 \cdot (\rho + \alpha_4 \cdot \rho_x)}} \tag{7}$$

When, in Equation (7), the invariables $C_2$, $C_4$, $I_2$, $I_4$, $\alpha_2$, $\alpha_4$ and $\rho$ are evaluated in advance, the density $\rho_x$ of the fluid to be measured can be found from the processing of $f_4/f_2$. The arithmetic circuit 6 executes the processing for obtaining $\rho_x$ from the received signals relevant to $f_2$ and $f_4$.

The density meter of this construction evaluates the density $\rho_x$ on the basis of Equation (7) which is not affected by the Young's modulus. In principle, therefore, the vibrator 1 suffers no error resulting from a change in its Young's modulus E. Accordingly, the vibrator can be made of a highly corrosion-resisting material whose Young's modulus E exhibits a large temperature coefficient.

The vibrator 1 shown in FIG. 6 is in the shape of a plate which is fixed at both ends. In this case, a force F applied in the axial direction of the vibrator 1 can be measured.

When such a flat vibrator is vibrated in, for example, the two vibration modes of the first order and the second order, the natural frequency $f_1$ concerning the first order vibration mode and the natural frequency $f_2$ concerning the second order vibration mode are expressed by Equations (8) as functions of the force F:

$$f_1 = C_1 \sqrt{\frac{E \cdot I}{\rho \cdot A \cdot l^4 (1 + \alpha_1 \cdot h)} + \frac{\beta_1 \cdot F}{\rho \cdot A \cdot l^2 (1 + \alpha_1 \cdot h)}} \quad (8)$$

$$f_2 = C_2 \sqrt{\frac{E \cdot I}{\rho \cdot A \cdot l^4 (1 + \alpha_2 \cdot h)} + \frac{\beta_2 \cdot F}{\rho \cdot A \cdot l^2 (1 + \alpha_2 \cdot h)}}$$

where $C_1$, $C_2$: constants which are respectively determined by the first order and second order vibration modes, $l$: length of the vibrator 1 (thin-walled portion), $I$: second moment of area of the vibrator 1 (thin-walled portion), $\alpha_1$, $\alpha_2$: constants which are respectively determined by the first order and second order vibration modes, $h$: $\rho_x/\rho$ ($\rho_x$ denotes the density of a fluid surrounding the vibrator 1), $\beta_1$, $\beta_2$: constants which are respectively determined by the first order and second order vibration modes, $F$: external force to be measured.

Here, $(f_1/C_1)^2 - (f_2/C_2)^2$ is evaluated as in Equation (9):

$$\left(\frac{f_1}{C_1}\right)^2 - \left(\frac{f_2}{C_2}\right)^2 = \frac{E \cdot I \cdot h}{\rho \cdot A \cdot l^4} \cdot (\alpha_2 - \alpha_1) + \quad (9)$$

$$\frac{F}{\rho \cdot A \cdot l^2} (\beta_1 \beta_2) + h (\beta_2 \cdot \alpha_2 - \beta_1 \cdot \alpha_1)$$

Assuming that the first and third terms on the right of Equation (9) are constant values, the external force to be measured F can be obtained by the use of this equation. In Equation (9), the value of the Young's modulus E varies depending upon the ambient temperature. When this influence is taken into consideration, the influence coefficient $\Delta_1$ can be expressed by Equation (10):

$$\Delta_1 = \frac{I \cdot h}{\rho \cdot A \cdot l^4} \cdot (\alpha_2 - \alpha_1) \quad (10)$$

On the other hand, when it is supposed that the vibrator 1 is vibrated in a single vibration mode of, for example, the first order as has been performed in the prior art, $(f_1/C_1)^2$ becomes as Equation (11):

$$\left(\frac{f_1}{C_1}\right)^2 = \frac{E \cdot I}{\rho \cdot A \cdot l^4 (1 + \alpha_1 \cdot h)} + \frac{\beta_1 \cdot F}{\rho \cdot A \cdot l^2 (1 + \alpha_1 \cdot h)} \quad (11)$$

The influence coefficient $\Delta_2$ of the Young's modulus in Equation (11) can be represented by Equation (12):

$$\Delta_2 = \frac{I}{\rho \cdot A \cdot l^4 (1 + \alpha_1 \cdot h)} \approx \frac{I}{\rho \cdot A \cdot l^4} \quad (\because \alpha_1 \cdot h << 1) \quad (12)$$

When comparisons are made between the influence coefficient $\Delta_1$ of the Young's modulus E in the case of two vibration modes as in the apparatus of this invention (Equation 10) and the influence coefficient $\Delta_2$ of the Young's modulus in the case of the single vibration mode as in the prior art (Equation 12)), the present invention lessens the influence of the Young's modulus E, and the improvement factor $\lambda_E$ is given by Equation (13):

$$\lambda_E = \frac{\Delta_1}{\Delta_2} \quad (13)$$

$$= h (\alpha_2 - \alpha_1)$$

The vibrator 1 shown in FIG. 7 comprises two parallel flat plates held by flexors 1F. In the following explanation, the parallel flat plate-vibrator is exposed to a fluid or gas whose temperature is to be measured.

When the vibrator of such construction is vibrated in the two vibration modes of, for example, the first order and the second order, the natural frequency $f_1$ concerning the first order vibration mode and the natural frequency $f_2$ concerning the second order vibration mode can be expressed by Equations (14) as functions of the temperature t:

$$f_1^2 = C_1 \cdot \frac{E_o}{\rho_p \left(1 + \beta_1 \cdot \frac{\rho_x}{\rho_p}\right)} \cdot \{1 + \alpha(t - t_o)\} \quad (14)$$

$$f_2^2 = C_2 \cdot \frac{E_o}{\rho_p \left(1 + \beta_2 \cdot \frac{\rho_x}{\rho_p}\right)} \cdot \{1 + \alpha(t - t_o)\}$$

where $t_o$: reference temperature, $E_o$: Young's modulus of the vibrator 1 (thin-walled portion at $t = t_o$, $\rho_p$: density of the vibrator 1 at $t = t_o$, $\alpha$: temperature coefficient of $E_o/\rho_p$, $\rho_x$: density of the fluid surrounding the vibrator 1.

When Equations (14) have the fluid density $\rho_x$ eliminated therefrom to derive an equation concerning the temperature t, Equation (15) is obtained:

$$t = \frac{1}{\alpha} \cdot \left\{ f_1^2 \cdot \frac{\rho_p}{C_1 \cdot E_o} \left( 1 + \beta_1 \cdot \frac{r^2 \cdot \frac{C_2}{C_1} - 1}{2 - \beta_1 \cdot r^2 \cdot \frac{C_2}{C_1}} \right) - 1 \right\} + t_o$$

where $r = f_1/f_2$

In Equation (15), all the quantities in the right-hand side are constants except $f_1$ and r, and r can be obtained from $f_1$ and $f_2$. Accordingly, the temperature t can be found by performing the arithmetic operations of Equation (15). In this case, the arithmetic circuit 6 executes the processing required by Equation (15).

Although the vibrator of FIG. 6 has been described as measuring a force and that of FIG. 7 as measuring a temperature, temperature may be measured using the vibrator of FIG. 6 and force may be measured with the vibrator of FIG. 7.

Figure 8:
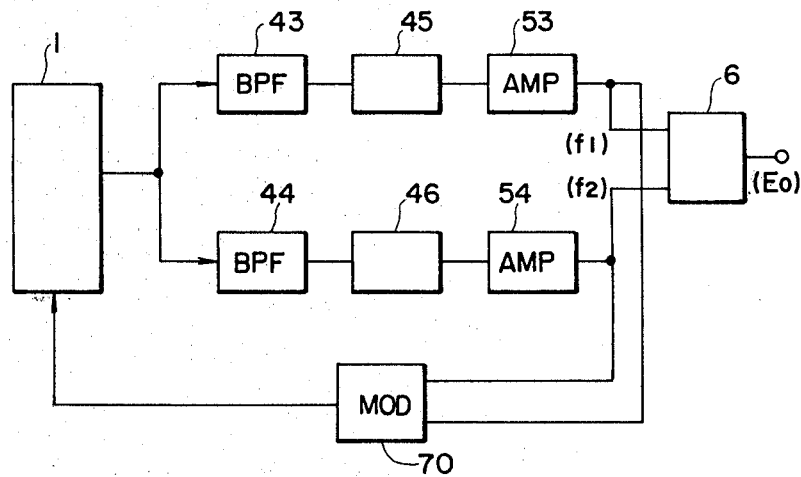
FIGS. 8 through 10 are schematic block diagrams each showing another embodiment of this invention.
Figure 9:
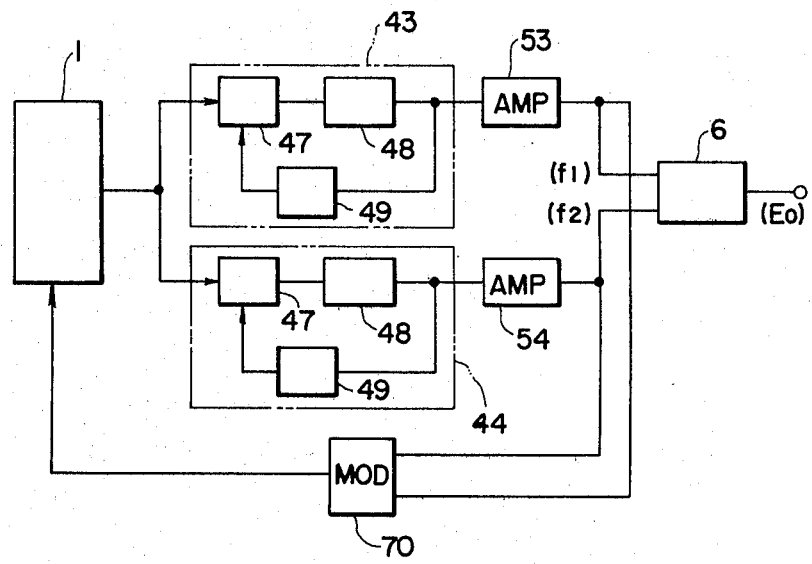
Figure 10:
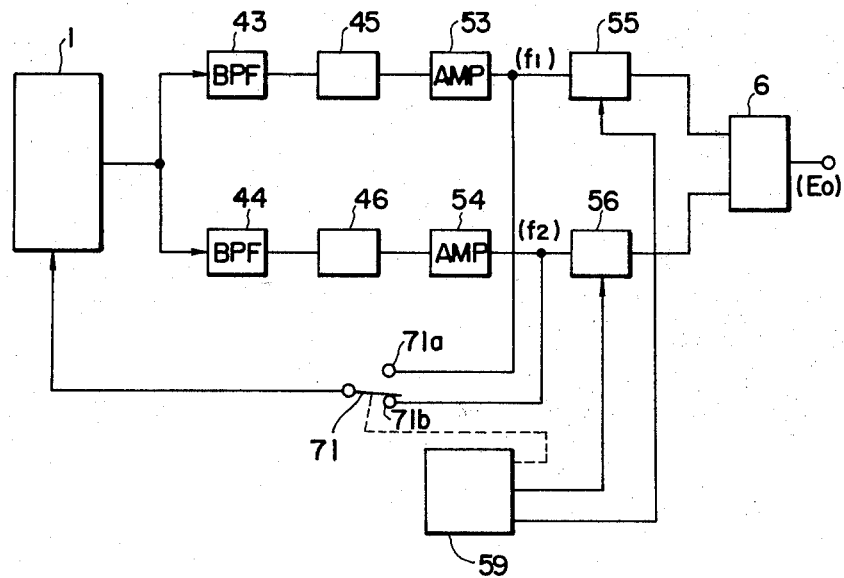

FIGS. 8 through 10 are schematic block diagrams showing other embodiments of this invention.

In the embodiment of FIG. 8, a signal associated with the vibration frequency of the vibrator 1 as derived from the vibrator 1 is applied to a band-pass filter 43 adapted to pass, for example, the frequency $f_1$ of the first order vibration mode and a band-pass filter 44 adapted to pass, for example the frequency $f_2$ of the second order vibration mode so as to obtain the frequency signals $f_1$ and $f_2$ in the two vibration modes through phase shifters 45 and 46 and amplifiers 53 and 54. Frequency signals $f_1$ and $f_2$ are applied to the vibrator 1 through a modulator 70 so as to continuously vibrate the vibrator 1 in the two vibration modes.

In the embodiment of FIG. 9 phase-locked loops (PLLs) whose capture ranges differ from each other are employed as the band-pass filters 43 and 44 in the circuit of FIG. 8. The PLL is constructed of a phase difference detector circuit 47, a low-pass filter 48 and a voltage-controlled oscillator 49. The closed loop formed of these circuits is operated so as to select and pass only input signals which have frequencies of or near the center frequency (capture range) of the voltage-controlled oscillator 49.

In the embodiment of FIG. 10, the outputs $f_1$ and $f_2$ of the amplifiers 53 and 54 are applied to the vibrator 1 through a switch 71, while they are also applied to the arithmetic circuit 6 through frequency signal-holding circuits 55 and 56, respectively. A control circuit 59 controls the switch 71 and the signal holding circuits 55 and 56, and the vibrator 1 is vibrated in the two vibration modes in time-division fashion.

In any of the embodiments of FIGS. 8 through 10, it is possible to employ a single vibration detector element and a single driver element for the vibrator 1. In addition, the circuits of the respective embodiments can employ the vibrators of FIGS. 5 through 7.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. A vibration type transducer comprising:
   a vibrator,
   vibration drive means for vibrating said vibrator in at least two vibration modes,
   at least two vibration detection means for detecting frequency signals corresponding to said vibration modes of said vibrator,
   an adder circuit coupled to said vibration detection means for adding said frequency signals of said vibration detecting means,
   a subtracter circuit coupled to said vibration detection means for subtracting said frequency signals of said vibration detection means, and
   an arithmetic circuit coupled to said adder circuit and said subtracter circuit for providing an output signal corresponding to a physical quantity to be measured.

2. A vibration type transducer according to claim 1, wherein said vibrator is in the shape of a cylinder having one end closed, means for introducing different pressures inside and outside said vibrator, said arithmetic circuit deriving a signal corresponding to a difference in said pressures.

3. A vibration type transducer according to claim 1, wherein said vibrator is in the shape of a cylinder having one end open, and a fluid to be measured is introduced around said vibrator, and said arithmetic circuit deriving the signal corresponding to the density of said fluid to be measured.

4. A vibration type transducer according to claim 1, wherein said vibrator is in the shape of a flat plate having both ends supported.

5. A vibration type transducer according to claim 1, wherein said vibrator is in the shape of two parallel flat plates having both ends supported.

6. A vibration type transducer according to claim 1, wherein a force to be measured is applied to said vibrator, said arithmetic circuit deriving a signal corresponding to said force.

7. A vibration type transducer according to claim 1, wherein said vibrator is exposed to a fluid or gas to be measured, and said arithmetic circuit deriving a signal corresponding to said fluid or gas surrounding said vibrator.

8. A vibration type transducer according to claim 1, wherein said vibration drive means and said vibration detection means are piezoelectric elements which are mounted on said vibrator.

* * * * *